United States Patent [19]

Crookes

[11] Patent Number: 4,521,431

[45] Date of Patent: Jun. 4, 1985

[54] AMINOALKYL FURAN DERIVATIVE

[75] Inventor: Derek L. Crookes, Hertford, England

[73] Assignee: Glaxo Group Limited, London, England

[21] Appl. No.: 406,710

[22] Filed: Aug. 9, 1982

Related U.S. Application Data

[63] Continuation of Ser. No. 307,575, Oct. 1, 1981, abandoned.

[30] Foreign Application Priority Data

Oct. 1, 1980 [GB] United Kingdom ............... 8031634

[51] Int. Cl.$^3$ ..................... A01K 31/34; C07D 307/52
[52] U.S. Cl. ..................................... 514/471; 549/495
[58] Field of Search ......................... 549/495; 424/285

[56] References Cited

U.S. PATENT DOCUMENTS 4,128,658  12/1978  Price et al. ........................ 424/285
4,279,819  7/1981   Price et al. ..................... 549/480 X Primary Examiner—Richard L. Raymond
Attorney, Agent, or Firm—Bacon & Thomas

[57] ABSTRACT

A novel crystal form of ranitidine (N-[2-[[[5-(dimethylamino)methyl]-2-furanyl]methyl]thio]ethyl-N'-methyl-2-nitro-1,1-ethenediamine) hydrochloride, designated Form 2, and having favorable filtration and drying characteristics, is characterized by its infra-red spectrum and/or by its x-ray powder diffraction patterns.

18 Claims, 1 Drawing Figure

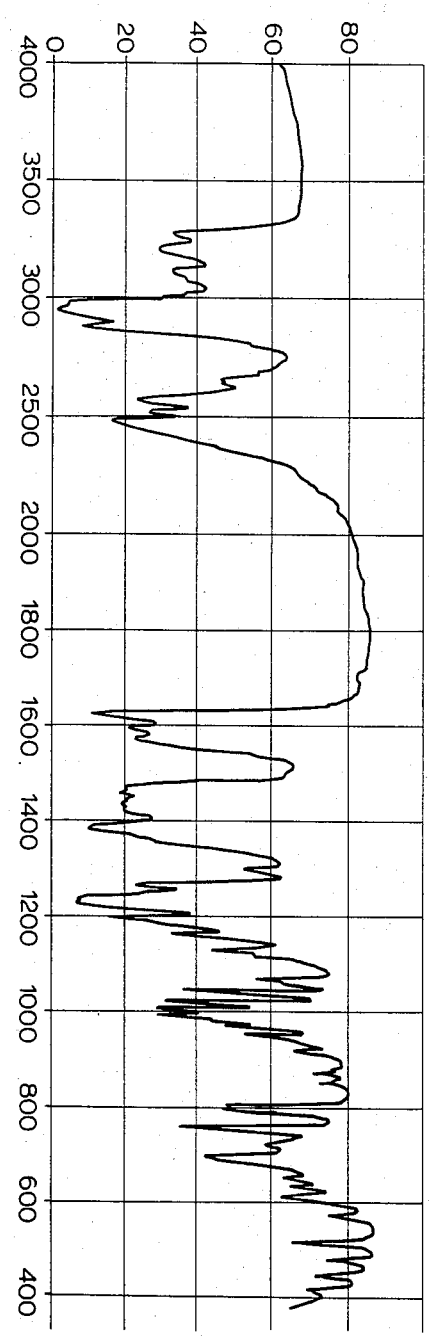

AMINOALKYL FURAN DERIVATIVE

This application is a continuation of application Ser. No. 307,575, filed Oct. 1, 1981, now abandoned.

The present invention is concerned with the hydrochloride salt of the $H_2$-antagonist N-[2-[[[5-(dimethylamino)methyl]-2-furanyl]methyl]thio]ethyl-$N^1$-methyl-2-nitro-1,1-ethenediamine, which has the approved name 'ranitidine', and its production and isolation.

Ranitidine, as described and claimed in British Pat. No. 1,565,966, shows potent histamine $H_2$-blocking activity and may be used in the treatment of conditions where there is an advantage in lowering gastric acidity, particularly in gastric and peptic ulceration, as a prophylactic measure in surgical procedures, and in the treatment of allergic and inflammatory conditions where histamine is a known mediator.

The hydrochloride salt of ranitidine (hereinafter referred to as ranitidine hydrochloride) is of particular importance since it enables ranitidine to be conveniently formulated in, for example, tablets for oral administration. There is thus the need to produce ranitidine hydrochloride in as pure and as highly crystalline a condition as possible in order to fulfil exacting pharmaceutical requirements and specifications.

The process by which the ranitidine hydrochloride is produced also needs to be one which is convenient to operate on a plant scale. In particular it is desirable that the hydrochloride should be prepared with concentrated hydrochloric acid and that the solvent for crystallisation should be readily recoverable.

In addition, the product should be in a form that is readily filtered off and easily dried. It is also desirable that, if required, the product can be recrystallised from the same solvent system.

Ranitidine hydrochloride has been obtained in a crystalline form, designated Form 1, by dissolving ranitidine in industrial methylated spirit containing hydrogen chloride and adding ethyl acetate to the solution, as described in the above mentioned British Patent specification. This procedure, however, does not have the desirable feature of a manufacturing process described above and Form 1 of the hydrochloride salt has unsuitable filtration and drying characteristics.

It has now been discovered that ranitidine hydrochloride can be prepared in a new crystalline form having more advantageous properties and the manufcturing process for the said new crystalline form fulfills the desirable features described above. The present invention thus provides ranitidine hydrochloride in a new crystalline form designated Form 2. Form 2 has been found generally to have larger crystals than the hitherto known Form 1 and exhibits more favourable filtration and drying characteristics. Furthermore, Form 2 is less hygroscopic than Form 1, which is an additional advantage in view of the sensitivity of ranitidine hydrochloride to moisture.

Form 2 ranitidine hydrochloride may be characterised by its infra-red spectrum in mineral oil and/or by its X-ray powder diffraction pattern. These will now be discussed in more detail.

INFRA-RED SPECTRUM

The infra-red spectrum of Form 2 ranitidine hydrochloride as a mull in mineral oil shows the following main peaks:

| | |
|---|---|
| 3260 | 1075 |
| 3190 | 1045 |
| 3100 | 1021 |
| 2560 | 1006 |
| 2510 | 991 |
| 2470 | 972 |
| 1620 | 958 |
| 1590 | 810 |
| 1570 | 800 |
| 1263 | 760 |
| 1230 | 700 |
| 1220 | 660 |
| 1195 | 640 |
| 1163 | 620 $cm^{-1}$ |
| 1130 | |

The infra-red spectrum of the product of Example 1 below obtained in this way is shown in the accompanying drawing in which the ordinate is the transmittance in % and the abscissa is the wavenumber in $cm^{-1}$.

X-RAY DIFFRACTION

The X-ray diffraction pattern of Form 2 ranitidine hydrochloride may be obtained by loading the material into a 0.3 mm diameter glass capillary and photographing the pattern by the Debye Scherrer method in a 114.6 mm diameter camera by exposure for 12 hours to $CoK_a$ radiation and for 3 hours to $CuK_a$ radiation (for 'd' <3 Å). The weighted mean values of X-ray wavelengths used for the calculations were $CuK_a$ 1.54171 Å and $CoK_a$ 1.79024 Å.

The X-ray powder diffraction pattern of Form 2 ranitidine hydrochloride in terms of 'd' spacings and relative intensities (I) is as follows (s=strong, m=medium, w=weak, v=very, d=diffuse):

| d (Å) | I | d (Å) | I |
|---|---|---|---|
| 10.73 | m | 3.40 | 22 vw |
| 6.50 | 3 vwd | 3.35 | 2 vwd |
| 6.15 | m | 3.25 | wd |
| 5.83 | s | 3.12 | 2 vw |
| 5.63 | 3 vwd | 3.04 | 2 vwd |
| 5.42 | s | 2.97 | 3 vwd |
| 5.06 | 2 vw | 2.93 | 3 vwd |
| 4.92 | w | 2.88 | 3 vwd |
| 4.59 | 2 vw | 2.81 | vwd |
| 4.40 | s | 2.72 | vwd |
| 4.28 | w | 2.66 | 3 vwd |
| 3.91 | wd | 2.47 | 2 vwd |
| 3.79 | s | 2.44 | vw |
| 3.71 | m | 2.34 | 2 vwd |
| 3.60 | vwd | 2.30 | 3 vwd |
| 3.46 | m | 2.21 | 2 vwd |

Form 2 ranitidine hydrochloride may be formulated for administration in any convenient way and the invention includes within its scope pharmaceutical compositions comprising Form 2 ranitidine hydrochloride adapted for use in human or veterinary medicine. Such compositions may be presented for use in a conventional manner with the aid of a pharmaceutically acceptable carrier or excipient and may also contain if required other active ingredients, e.g. $H_1$-antagonists. Thus the hydrochloride salt according to the invention may be formulated for oral, buccal, topical, parenteral, or rectal administration. Oral administration is preferred, particularly in the form of tablets and capsules.

For oral administration, the pharmaceutical composition may take the form of for example, tablets, capsules, powders, solutions, syrups or suspensions prepared by conventional means with acceptable excipients. For buccal administration the compositions may take the form of tablets or lozenges formulated in conventional manner.

Form 2 ranitidine hydrochloride may be formulated for parenteral administration by bolus injection or continuous infusion. Formulations for injection may be presented in unit dosage form in ampoules, or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water, before use.

Form 2 ranitidine hydrochloride may also be formulated in rectal compositions such as suppositories or retention enemas, e.g. containing conventional suppository bases such as cocoa butter or other glycerides.

For topical application, Form 2 ranitidine hydrochloride may be formulated as ointments, creams, gels, lotions, powders or sprays in a conventional manner.

For internal administration a convenient daily dosage regime of Form 2 ranitidine hydrochloride is 1 to 4 doses to the total of some 40 mg to 1.2 g per day, dependent upon the condition of the patient.

The present invention also provides a process for the preparation of Form 2 rantidine hydrochloride which comprises crystallising ranitidine hydrochloride from a solution thereof in a solvent under conditions which yield Form 2 ranitidine hydrochloride.

The precise conditions under which Form 2 ranitidine hydrochloride is formed may be empirically determined and it is only possible to give a number of methods which have been found to be suitable in practice.

Thus, for example, Form 2 ranitidine hydrochloride may be prepared by crystallisation under controlled conditions. In particular, it can be prepared either from the corresponding free base by reaction with hydrochloric acid or by recrystallisation of previously isolated ranitidine hydrochloride. In general the use of a hydroxylic solvent, e.g. a lower alkanol, is preferred. In order to dissolve the starting material it may be helpful to warm and/or to include some water in the solvent system. In some cases it is necessary to add further organic solvent or a specific anti-solvent such as acetone in order to bring the Form 2 crystals out of solution.

When the starting material for the preparation of the desired Form 2 ranitidine hydrochloride is the free base, one preferred preparation involves treating a solution of ranitidine in propan-2-ol with hydrochloric acid, followed by crystallisation of the required form of the hydrochloride salt, preferably at an elevated temperature at up to 70° C., e.g. 40° to 60° C., particularly 48°-52° C., by addition of further quantities of propan-2-ol. Alternatively a solution of ranitidine in 2-methylpropan-2-ol, butan-2-ol or ethanol can be treated with hydrochloric acid and the desired Form 2 ranitidine hydrochloride crystallised at a temperature up to 70° C., for example from room temperature to 60° C. It is preferable to use concentrated hydrochloric acid (e.g. 35 to 38% w/w) and, in general, molar equivalent proportions of hydrochloric acid and ranitidine should be employed. Under these conditions, salt formation, as well as crystallisation, should preferably be carried out at an elevated temperature, for example within the above mentioned temperature ranges. It has been found that it may be advantageous to include in the starting solution, a small amount to water, additional to that in the hydrochloric acid e.g. up to 7%, preferably about 3% v/v. For example where ethanol is the solvent, this can be used in the form of industrial methylated spirit which contains about 2% v/v water.

When the starting material is ranitidine hydrochloride e.g. Form 1 or Form 2, the desired Form 2 salt may be crystallised using similar conditions for crystallisation to those described above. Alternatively, the salt may be dissolved, e.g. by warming, in an organic solvent such as methanol or ethanol followed by cooling of the resulting solution, e.g. to 10° to 40° C., and stirring until crystallisation of the required form is complete. In the case of some solvents, e.g. methanol, it may be advantageous to add a miscible anti-solvent such as acetone or ethyl acetate to the solution to complete crystallisation.

It has frequently been found desirable to add 'seeds' of Form 2 ranitidine hydrochloride to the crystallisation solution in order to induce crystallisation.

Form 2 ranitidine hydrochloride has proved to be readily isolable and can be filtered off from the crystallisation medium, if desired after cooling, and washed and dried.

If desired, the Form 2 ranitidine hydrochloride prepared as above may further be recrystallised using similar conditions for crystallisation to those described above.

In order that the invention may be more fully understood the following Examples are given by way of illustration only. All temperatures are in °C. The concentrated hydrochloric acid is 35% w/w and the industrial methylated spirit is 74° o.p. and contains 2% v/v water.

EXAMPLE 1 PREPARATION OF FORM 2 RANITIDINE HYDROCHLORIDE

One equivalent (about 5.3 ml) of concentrated hydrochloride acid was added to a solution of ranitidine (20 g) in a mixture of propan-2-ol (130 ml) and water (4 ml) at 45°. The mixture was heated at 50° whilst a further quantity of propan-2-ol (68 ml) was added and the resulting solution was then stirred at 50° to allow the product to crystallise. The slurry was cooled to 10° to 12° and the product was filtered off, washed with propan-2-ol (2×27 ml) and dried at 50° under reduced pressure to give Form 2 ranitidine hydrochloride (21 g) m.p. 139°-141°.

EXAMPLE 2 RECRYSTALLISATION OF RANITIDINE HYDROCHLORIDE

Form 2 ranitidine hydrochloride (25 g) was warmed in a mixture of propan-2-ol (66 ml) and water (9 ml) and the resulting solution was stirred at 50°. A further quantity of propan-2-ol (150 ml) was added over a period of 5 to 10 minutes and the product was allowed to crystallise at 50°. The slurry was cooled to 10° to 12° and the product was filtered off, washed with propan-2-ol (2×30) and dried at 50° under reduced pressure to give Form 2 ranitidine hydrochloride (23.6 g) m.p. 139°-141°.

EXAMPLE 3 RECRYSTALLISATION OF RANITIDINE HYDROCHLORIDE

Form 2 ranitidine hydrochloride (50 g) was warmed in a mixture of propan-2-ol (132 ml) and water (18 ml) and the resulting solution stirred at 55°. A further quantity of propan-2-ol (300 ml) was added over a period of 5 to 10 minutes and the product was allowed to crystallise at 55°. The slurry was cooled to 10° to 12° and the product was filtered off, washed with propan-2-ol (2×60 ml) and dried at 50° under reduced pressure to give Form 2 ranitidine hydrochloride (48 g) m.p. 141°–142°.

EXAMPLE 4 RECRYSTALLISATION OF RANITIDINE HYDROCHLORIDE

Form 2 ranitidine hydrochloride (50 g) was dissolved in industrial methylated spirit (200 ml) at 70°. The solution was allowed to cool and the product crystallised out at 40°. The resulting slurry was cooled to 0° and the product was filtered off, washed with industrial methylated spirit (20 ml) and dried at 50° under reduced pressure to give Form 2 ranitidine hydrochloride (47.7 g) m.p. 140°–142°.

EXAMPLE 5 PREPARATION OF FORM 2 RANITIDINE HYDROCHLORIDE

Concentrated hydrochloric acid (1.4 ml) was added to a solution of ranitidine (6 g) in 2-methylpropan-2-ol. The mixture was stirred at 40° to allow the product to crystallise and the resulting slurry was cooled to 20°. Further concentrated hydrochloric acid (about 0.2 ml) was added to the mixture and, after stirring for 1 h at 20° the product was filtered off, washed with 2-methylpropan-2-ol, and dried at 50° under reduced pressure to give Form 2 ranitidine hydrochloride (5.96 g) m.p. 141°–142°.

EXAMPLE 6 PREPARATION OF FORM 2 RANITIDINE HYDROCHLORIDE

The process of Example 5 was repeated, using butan-2-ol instead of 2-methylpropan-2-ol and stirring the mixture at 55°, to give Form 2 ranitidine hydrochloride (6.1 g) m.p. 140°–141°.

EXAMPLE 7 RECRYSTALLISATION OF FORM 1 RANITIDINE HYDROCHLORIDE TO GIVE FORM 2 RANITIDINE HYDROCHLORIDE

Form 1 ranitidine hydrochloride (25 g) was warmed in a mixture of propan-2-ol (66 ml) and water (9 ml) and the resulting solution was stirred at 50°. A further quantity of propan-2-ol (150 ml) was added over a period of 5 to 10 minutes and the product was allowed to crystallise at 50°. The slurry was cooled to 10° to 12° and the product was filtered off, washed with propan-2-ol (2×30 ml) and dried at 50° under reduced pressure to give Form 2 ranitidine hydrochloride (22.7 g) m.p. 139°–140°.

EXAMPLE 8 RECRYSTALLISATION OF FORM 1 RANITIDINE HYDROCHLORIDE TO GIVE FORM 2 RANITIDINE HYDROCHLORIDE

Form 1 ranitidine hydrochloride (10 g) was warmed in a mixture of methanol (15 ml) and acetone (15 ml). The solution was stirred at 50° whilst a further quantity of acetone (45 ml) was added and the resulting solution was then stirred at 50° to allow the product to crystallise. The slurry was cooled to 20° and the product was filtered off, washed with acetone (2×10 ml), and dried at 50° under reduced pressure to give Form 2 ranitidine hydrochloride (9.5 g) m.p. 141°–142°.

EXAMPLE 9 PREPARATION OF FORM 2 RANITIDINE HYDROCHLORIDE

Ranitidine (6 g) was dissolved in industrial methylated spirits (42 ml) at ambient temperature (about 20°). One equivalent (about 1.6 ml) of concentrated hydrochloric acid was added to the solution. The temperature rose to about 27° and the solution was seeded at this temperature to induce crystallisation. The product crystallised to give a thick slurry at 25°–27°. After 0.5 h the slurry was cooled to 10°–12° for 0.5 h. The product was then filtered off, washed with industrial methylated spirits (5 ml) and dried at 50° under reduced pressure to give Form 2 ranitidine hydrochloride (5.4 g) m.p. 139°–140°.

EXAMPLES 10-12 PREPARATION OF FORM 2 RANITIDINE HYDROCHLORIDE

Ranitidine (50 g) was dissolved in propan-2-ol (225 ml) at 45°–55°. Celite (0.6 g) was added and the reaction mixture filtered. Propan-2-ol (100 ml) heated to 45°–55° was used to wash the filter. Water (see following Table—omitted in Example 12) was added to the combined filtrate and the reaction solution adjusted to the crystallisation temperature (see table).

Concentrated hydrochloric acid (approximately 14 ml) was added until the end-point was reached i.e. an aliquot of the reaction mixture turned bromothymol blue from green to yellow. Propan-2-ol (168 ml) warmed to 45°–55° was added and the temperature of the solution adjusted to the crystallisation temperature chosen. The solution was seeded with Form 2 ranitidine hydrochloride, if necessary, and left to stir for 3 hours.

The reaction mixture was then cooled to room temperature and stirred overnight. Prior to filtration the mixture was cooled to 8°–12° for 1½ hours. The mixture was filtered and the product washed with cold (8°–12°) propan-2-ol (2×62 ml). The Form 2 ranitidine hydrochloride product was dried in a vacuum oven at 50°.

TABLE

| Example No. | Vol. of Water added (ml) | Crystallisation Temp. (°C.) | Yield (g) |
| --- | --- | --- | --- |
| 10 | 2.1 | 40 | 52.2 |
| 11 | 2.1 | 55 | 51.0 |
| 12 | — | 50 | 54.0 |

I claim:

1. Form 2 ranitidine hydrochloride characterised by an infra-red spectrum as a mull in mineral oil showing the following main peaks:

| | |
| --- | --- |
| 3260 | 1075 |
| 3190 | 1045 |
| 3100 | 1021 |
| 2560 | 1006 |
| 2510 | 991 |
| 2470 | 972 |
| 1620 | 958 |
| 1590 | 810 |
| 1570 | 800 |
| 1263 | 760 |
| 1230 | 700 |
| 1220 | 660 |
| 1195 | 640 |
| 1163 | 620 cm$^{-1}$ |
| 1130 | |

2. Form 2 ranitidine hydrochloride according to claim 1 further characterised by the following x-ray powder diffraction pattern expressed in terms of "d" spacings and relative intensities (1) (s=strong, m=medium, w=weak, v=very, d=diffuse) and obtained by the Debye Scherrer method in a 114.6 mm diameter camera by exposure for 12 hours to CoK$_a$ radiation and for 3 hours to CuKa radiation:

| d (Å) | I | d (Å) | I |
|-------|------|-------|------|
| 10.73 | m | 3.40 | 2 w |
| 6.50 | 3 vwd | 3.35 | 2 vwd |
| 6.13 | m | 3.25 | wd |
| 5.83 | s | 3.12 | 2 vw |
| 5.63 | 3 vwd | 3.04 | 2 vwd |
| 5.42 | s | 2.97 | 3 vwd |
| 5.06 | 2 vw | 2.93 | 3 vwd |
| 4.92 | w | 2.88 | 3 vwd |
| 4.59 | 2 vw | 2.81 | vwd |
| 4.40 | s | 2.72 | vwd |
| 4.28 | w | 2.66 | 3 vwd |
| 3.91 | wd | 2.47 | 2 vwd |
| 3.79 | s | 2.44 | vw |
| 3.71 | m | 2.34 | 2 vwd |
| 3.60 | vwd | 2.30 | 3 vwd |
| 3.46 | m | 2.21 | 2 vwd |

3. A pharmaceutical composition in the form of tablets comprising Form 2 ranitidine hydrochloride as defined in claim 1 together with at least one inert pharamceutically acceptable carrier or diluent.

4. A pharmaceutical composition in the form of tablets comprising Form 2 ranitidine hydrochloride as defined in claim 2 together with at least one inert pharmaceutically acceptable carrier or diluent.

5. A pharmaceutical composition in the form of capsules comprising Form 2 ranitidine hydrochloride as defined in claim 1 together with at least one inert pharmaceutically acceptable carrier or diluent.

6. A pharmaceutical composition in the form of capsules comprising Form 2 ranitidine hydrochloride as defined in claim 2 together with at least one inert pharmaceutically acceptable carrier or diluent.

7. A pharmaceutical composition in the form of a powder comprising Form 2 ranitidine hydrochloride as defined in claim 1 together with at least one inert pharmaceutically acceptable carrier or diluent.

8. A pharmaceutical composition in the form of a powder comprising Form 2 ranitidine hydrochloride as defined in claim 2 together with at least one inert pharmaceutically acceptable carrier or diluent.

9. A pharmaceutical composition in the form of lozenges comprising Form 2 ranitidine hydrochloride as defined in claim 1 together with at least one inert pharmaceutically acceptable carrier or diluent.

10. A pharmaceutical composition in the form of lozenges comprising Form 2 ranitidine hydrochloride as defined in claim 2 together with at least one inert pharmaceutically acceptable carrier or diluent.

11. A pharmaceutical composition in the form of suppositories comprising Form 2 ranitidine hydrochloride as defined in claim 1 together with at least one inert pharmaceutically acceptable carrier or diluent.

12. A pharmaceutical composition in the form of suppositories comprising Form 2 ranitidine hydrochloride as defined in claim 2 together with at least one inert pharmaceutically acceptable carrier or diluent.

13. A pharmaceutical composition in the form of retention enemas comprising Form 2 ranitidine hydrochloride as defined in claim 1 together with at least one inert pharmaceutically acceptable carrier or diluent.

14. A pharmaceutical composition in the form of retention enemas comprising Form 2 ranitidine hydrochloride as defined in claim 2 together with at least one inert pharmaceutically acceptable carrier or diluent.

15. A pharmaceutical composition in the form of an ointment comprising Form 2 ranitidine hydrochloride as defined in claim 1 together with at least one inert pharmaceutically acceptable carrier or diluent.

16. A pharmaceutical composition in the form of an ointment comprising Form 2 ranitidine hydrochloride as defined in claim 2 together with at least one inert pharmaceutically acceptable carrier or diluent.

17. A method of treating condition mediated through histamine H$_2$-receptors which comprises administering to a patient an effective amount of a compound as claimed in claim 1 to relieve said condition.

18. A method of treating condition mediated through histamine H$_2$-receptors which comprises administering to a patient an effective amount of a compound as claimed in claim 2 to relieve said condition.

* * * * *